(12) United States Patent
Franciskovich et al.

(10) Patent No.: US 8,945,837 B2
(45) Date of Patent: Feb. 3, 2015

(54) STERILIZATION INDICATOR INCLUDING A SIMPLIFIED GENETICALLY ENGINEERED BIOLOGICAL INDICATOR

(71) Applicant: American Sterilizer Company, Mentor, OH (US)

(72) Inventors: Phillip P. Franciskovich, Concord, OH (US); Tricia A. Cregger, Fairlawn, OH (US); William A. Yirava, Willoughby, OH (US)

(73) Assignee: American Sterilizer Company, Mentor, OH (US)

( * ) Notice: Subject to any disclaimer, the term of this patent is extended or adjusted under 35 U.S.C. 154(b) by 95 days.

(21) Appl. No.: 13/832,019

(22) Filed: Mar. 15, 2013

(65) Prior Publication Data

US 2014/0273072 A1 Sep. 18, 2014

(51) Int. Cl.
*C12N 1/20* (2006.01)
*C12Q 1/22* (2006.01)
*C12N 15/75* (2006.01)
*C12N 15/74* (2006.01)

(52) U.S. Cl.
CPC *C12Q 1/22* (2013.01); *C12N 15/75* (2013.01); *C12N 15/74* (2013.01)
USPC .......................................... 435/6.1; 435/252.1

(58) Field of Classification Search
None
See application file for complete search history.

(56) References Cited

U.S. PATENT DOCUMENTS

| | | | |
|---|---|---|---|
| 5,723,330 | A | 3/1998 | Rees et al. |
| 6,187,555 | B1 | 2/2001 | Tautvydas |
| 6,942,989 | B2 | 9/2005 | Felkner et al. |
| 7,326,562 | B2 | 2/2008 | Felkner et al. |
| 2008/0070231 | A1 | 3/2008 | Franciskovich et al. |
| 2012/0183995 | A1 | 7/2012 | Ferrari et al. |

FOREIGN PATENT DOCUMENTS

WO 01/10881 2/2001

OTHER PUBLICATIONS

Luiz Carlos Martins das Neves et al.; "Biomonitoring of biosurfactant production by green fluorescent protein-marked *Bacillus subtilis* W1012"; J Chem Technol Biotechnol 2009; 84: 112-118.
Chris D. Webb et al.; "Use of Green Fluorescent Protein for Visualization of Cell-Specific Gene Expression and Subcellular Protein Localization during Sporulation in *Bacillus subtilis*"; Journal of Bacteriology, vol. 177, No. 20; Oct. 1995; pp. 5906-5911.
Barbara Hartl et al.; "Development of a New Integration Site within the *Bacillus subtilis* Chromosome and Construction of Compatible Expression Cassettes"; Journal of Bacteriology, vol. 183, No. 8; Apr. 2001; pp. 2696-2699.
Tingting Xu et al.; "Genetically modified whole-cell bioreporters for environmental assessment"; Ecological Indicators (2012); pp. 1-17.
Lars Hestbjerg Hansen et al.; "Detection of Oxytetracycline Production by *Streptomyces rimosus* in Soil Microcosms by Combining Whole-Cell Biosensors and Flow Cytometry"; Applied and Environmental Microbiology, vol. 67, No. 1, Jan. 2001, pp. 239-244.
Amit P. Bhavsar et al.; "Development and Characterization of a Xylose-Dependent System for Expression of Cloned Genes in *Bacillus subtilis*: Conditional Complementation of a Teichoic Acid Mutant"; Applied and Environmental Microbiology, vol. 67, No. 1, Jan. 2001, pp. 403-410.
Joe Hinnebusch et al.; "Linear plasmids and chromosomes in bacteria"; Molecular Microbiology (1993) 10(5), pp. 917-922.
Yun-Peng Chao et al.; "Applicability of New Expression Vectors for Both Engineering Uses and Biological Studies", Biotechnol. Prog. 2003, 19, pp. 1076-1080.
Ben Fan et al.; "Efficient colonization of plant roots by the plant growth promoting bacterium *Bacillus amyloliquefaciens* FZB42, engineered to express green fluorescent protein"; Journal of Biotechnology 151 (2011), pp. 303-311.
Patrick Kirchner et al.; "Monitoring the microbicidal effectiveness of gaseous hydrogen peroxide in sterilisation processes by means of a calorimetic gas sensor"; Food Control 31 (2013), pp. 530-538.
H. Albert et al: "Biological indicators for steam sterilization: characterization of a rapid biological indicator utilizing *Bacillus stearothermophilus* spore-associated alpha-glucosidase enzyme"; Journal of Applied Microbiology, vol. 85, No. 5, Nov. 1, 1998; pp. 865-874.
PCT/US2014/017903; PCT International Search Report and Written Opinion of the International Searching Authority dated Jun. 2, 2014.

*Primary Examiner* — Michele K Joike
(74) *Attorney, Agent, or Firm* — Renner, Otto, Boisselle & Sklar, LLP

(57) ABSTRACT

A sterilization indicator, including a first compartment containing a genetically engineered biological indicator, and a second compartment containing an enzyme substrate, the second compartment adapted to maintain the enzyme substrate separate from the biological indicator during sterilization, and to permit the enzyme substrate to contact the biological indicator after the biological indicator has been exposed to the sterilization medium; in which the genetically engineered biological indicator comprises at least one test organism and at least one reporter gene suitable for producing an indicator enzyme, the reporter gene being taken up by the test organism; and the test organism is free of any active or activatable repressor gene that would inhibit expression of the reporter gene if present in the test organism or sterilization indicator, and the indicator enzyme and the enzyme substrate are selected such that enzymatic action of the indicator enzyme upon the enzyme substrate yields a detectable signal.

15 Claims, 2 Drawing Sheets

STERILIZATION INDICATOR INCLUDING A SIMPLIFIED GENETICALLY ENGINEERED BIOLOGICAL INDICATOR

BACKGROUND

The present inventors previously disclosed a genetically engineered biological indicator comprising at least one test organism and at least one reporter gene for producing an indicator enzyme, the reporter gene being taken up by the test organism, the test organism comprising bacterial spores; and at least one repressor gene that inhibits expression of the reporter gene until the reporter gene is exposed to at least one inducer; wherein the genetically engineered biological indicator is a component of a self-contained biological indicator, e.g., a two compartment system such as a vial and cap combination, the two compartment system further containing a growth medium for the genetically engineered biological indicator. See, e.g., U.S. Pat. No. 8,372,624.

In the genetically engineered biological indicator system and method disclosed in U.S. Pat. No. 8,372,624, the repressor gene inhibits expression of the reporter gene until the system is exposed to the inducer. Various problems have been encountered in use of this system and method, including discoloration of the indicator due to degradation of the inducer and/or issues relating to the repressor gene which, like the reporter gene, must be taken up by the test organism. The discoloration has been observed, for example, when the system is heated during the sterilization process or in processing to produce the genetically engineered biological indicator system. It is believed that the inducer, e.g., xylose, is degraded by the heating or other sterilization process (e.g., by oxidative sterilization processes, such as vapor hydrogen peroxide, ethylene oxide, etc.) and turns brown or is otherwise discolored. This browning or discoloration results in interference with detecting any change associated with a result showing the failure of the sterilization. This is, understandably, undesirable, since it results in reduced sensitivity of the test. The inducer was previously required to overcome the effects of the repressor gene. By omitting the repressor gene, there is no longer any need to use the inducer, and thus the browning or discoloration problem resulting from the inducer can be avoided. In addition, as will be recognized, the necessity to include the repressor gene in the vector used to induce the test organism to take up the reporter gene only increases the complexity of the overall process used to manufacture the genetically engineered biological indicator system. These problems have remained in need of a solution.

SUMMARY

Thus, problems have been encountered with use of this system, and the present inventors have addressed this problem by developing the present invention. The present inventors have developed a new genetically engineered biological indicator which includes, like the previous system, the at least one test organism and the at least one reporter gene for producing an indicator enzyme, the reporter gene being taken up by the test organism, the test organism comprising bacterial spores; wherein the genetically engineered biological indicator is a component of a self-contained biological indicator. However, the present invention does not require, and in fact excludes, the repressor gene and the inducer, which were required by the genetically engineered biological indicator system and method disclosed in U.S. Pat. No. 8,372,624.

Thus, in accordance with an embodiment of the present invention, there is provided a sterilization indicator, comprising:

a first compartment containing a genetically engineered biological indicator, the first compartment being adapted to permit the biological indicator to be brought into contact with a sterilization medium during sterilization; and a second compartment containing at least one enzyme substrate, the second compartment being adapted to maintain the enzyme substrate separate from the biological indicator during sterilization, and the second compartment being adapted to permit the enzyme substrate to contact the biological indicator after the biological indicator has been exposed to the sterilization medium;

wherein the genetically engineered biological indicator comprises at least one test organism and at least one reporter gene suitable for producing an indicator enzyme, the reporter gene being taken up by the test organism;

wherein the test organism in the sterilization indicator is free of any active or activatable repressor gene that would inhibit expression of the reporter gene if present in the test organism or sterilization indicator, and wherein the indicator enzyme and the enzyme substrate are selected such that enzymatic action of the indicator enzyme upon the enzyme substrate yields a detectable signal.

In one embodiment, the reporter gene is taken up by the test organism using at least one plasmid and/or at least one virus.

In one embodiment, the test organism comprises spores of *Geobacillus stearothermophilus* and/or *Bacillus atrophaeus*.

In one embodiment, the reporter gene comprises lacZ, bgaB, xylE, cat or a mixture of two or more thereof.

In one embodiment, the indicator enzyme comprises beta-D-galactosidase, beta-D-glucosidase, alpha-D-glucosidase, alkaline phosphatase, acid phosphatase, butyrate esterase, caprylate esterase lipase, chloroamphenicol acetylransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof.

In one embodiment, the reporter gene comprises lacZ or bgaB and the indicator enzyme comprises beta-D-galactosidase.

In one embodiment, the plasmid comprises a reporter gene and is free of any repressor gene.

In one embodiment, the virus comprises at least one gene transporter that comprises nucleic acid surrounded by a capsid, the gene transporter comprising a reporter gene and being free of any repressor gene. In one embodiment, the virus comprises at least one bacteriophage. In one embodiment, the virus comprises lambda or M13 bacteriophage.

In accordance with another embodiment of the present invention, there is provided a sterilization indicator, comprising:

a first compartment containing a genetically engineered biological indicator, the first compartment being adapted to permit the biological indicator to be brought into contact with a sterilization medium during sterilization; and a second compartment containing at least one enzyme substrate, the second compartment being adapted to maintain the enzyme substrate separate from the biological indicator during sterilization, and the second compartment being adapted to permit the enzyme substrate to contact the biological indicator after the biological indicator has been exposed to the sterilization medium;

wherein the genetically engineered biological indicator comprises spores of *Geobacillus stearothermophilus* and/or *Bacillus atrophaeus* and at least one reporter gene selected from lacZ, bgaB, xylE and cat for producing an indicator enzyme, the reporter gene being taken up by the spores of *Geobacillus stearothermophilus* and/or *Bacillus atrophaeus;* wherein the spores of *Geobacillus stearothermophilus* and/or *Bacillus atrophaeus* in the sterilization indicator are free of any active or activatable repressor gene that would inhibit expression of the reporter gene if present in the test organism or sterilization indicator, and wherein the indicator enzyme and the enzyme substrate are selected such that enzymatic action of the indicator enzyme upon the enzyme substrate yields a detectable signal.

In one embodiment, the indicator enzyme comprises beta-D-galactosidase, beta-D-glucosidase, alpha-D-glucosidase, alkaline phosphatase, acid phosphatase, butyrate esterase, caprylate esterase lipase, chloroamphenicol acetylransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof.

In accordance with another embodiment of the present invention, there is provided a sterilization process, comprising:

exposing an article to be sterilized and the sterilization indicator described above to a sterilization medium;

combining contents of the first compartment and the second compartment;

incubating the combined contents of the first compartment and the second compartment; and determining efficacy of the sterilization process by detecting the presence or absence of the detectable signal following the incubating.

In one embodiment, in the sterilization process, the sterilization medium comprises steam, dry heat, radiation, plasma, one or more gaseous sterilants and/or one or more liquid sterilants.

In one embodiment, in the sterilization process, the sterilization medium comprises electron beam radiation, electromagnetic radiation, gamma radiation, beta radiation, ethylene oxide, gaseous hydrogen peroxide, liquid hydrogen peroxide, formalin, glutaraldehyde, and/or peracetic acid.

The present invention may provide one or more of several advantages over the system of U.S. Pat. No. 8,372,624. By removing the repressor gene or otherwise knocking out its activity, the need for the inducer is also removed. 'Knocking out' the activity of a gene may be accomplished by insertion mutations, deletion mutations or by re-transforming the wild-type host organism with a virus or plasmid that doesn't contain that gene. Since the inducer, e.g., xylose, can inadvertently interfere with the proper function of the system of U.S. Pat. No. 8,372,624 in some cases, its removal eliminates this possibility altogether. By removing the repressor gene the present invention also provides the benefits of reduced cost and reduced complexity of manufacturing the sterilization indicator including the genetically engineered biological indicator, since neither the repressor nor the inducer are required components. By removing the repressor, the transfection vector can express its reporter enzyme constitutively; meaning that in the absence of repression the product of the reporter gene will be made to much higher levels thus increasing sensitivity of the indicator. Thus, the number and complexity of the steps involved in the manufacture of this sterilization indicator, and the cost and handling of these now-unnecessary components are eliminated. Finally, the absence of absorbance caused by degraded inducer further increases the sensitivity and signal intensity in the reader, when the sterilization indicator has been through the sterilization process, has been incubated and the results are determined.

BRIEF DESCRIPTION OF DRAWINGS

The present invention may be useful with a variety of sterilization indicator apparatus. The annexed drawings are intended to provide an exemplary, non-limiting depiction of a suitable sterilization apparatus, for the purpose of providing a better understanding of the invention, and are not intended to be limiting in any way. In the annexed drawings, like parts and features have like references.

It should be appreciated that for simplicity and clarity of illustration, elements shown in the Figures have not necessarily been drawn to scale. For example, the dimensions of some of the elements may be exaggerated relative to each other for clarity. Further, where considered appropriate, reference numerals have been repeated among the Figures to indicate corresponding elements.

Furthermore, it should be appreciated that the process steps and structures described below may not form a complete process flow for producing an end-useable sterilization indicator. The present invention can be practiced in conjunction with apparatus and processing techniques currently used in the art, and only so much of the commonly practiced process steps are included as are necessary for an understanding of the present invention.

DETAILED DESCRIPTION

The term "sterilization" refers to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term sterilization may be used herein to also refer to methods and procedures less rigorous than sterilization, for example, disinfection, sanitization, and the like. The genetically engineered biological indicator and the processes and apparatus described herein may be used in health care fields, scientific fields, and the like. These may be used in commercial and industrial applications where sterilization, disinfection, sanitization, decontamination, cleaning, and the like, may be desired. The commercial and industrial applications may include processes such as food processing, pasteurization, soil remediation, water remediation, and the like.

The sterilization process for which the disclosed sterilization indicator may be used may comprise any sterilization process. The sterilization process may include sterilization processes wherein the sterilization medium or sterilant may comprise steam, dry heat, radiation, plasma, as well as one or more gaseous sterilants, one or more liquid sterilants, and the like. The radiation may comprise electron beam or any electromagnetic spectra including ionizing radiation, pulsed white or ultraviolet light, microwave, and the like. The radiation may comprise gamma or beta radiation. The gaseous sterilants may comprise ethylene oxide, gaseous hydrogen peroxide, and the like. The liquid sterilants may comprise formalin (formaldehyde gas dissolved in water and optionally containing methanol to inhibit the formation of toxic substances), glutaraldehyde, peracetic acid, liquid hydrogen peroxide, and the like.

The genetically engineered biological indicator may be used to examine the lethality of sterilants against any target microorganism with less resistance to the sterilization process than the test organism provided with the genetically engineered biological indicator. These target microorganisms may include bacteria such as *Escherichia coli, Legionella* sp., *Campylobacter* sp., and other enteric bacteria, as well as *Staphylococcus* and *Streptococcus* species and other human pathogenic microorganisms such as *Cryptosporidium*.

The growth of an organism may comprise the combined result of a multitude of cellular processes. In typical sterilization indicator applications this may be observed in several ways. As cells grow and divide their individual numbers increase to a point at which the support medium of the cells may change from clear to cloudy to opaque (turbid). To facilitate the observation of growth, a pH indicator dye may be used. Growth requires energy. This energy may be provided by the ability of the cell to metabolize nutrients contained in the support medium. The breakdown products of this process may cause the support medium to become acidic. This acidity may induce a pH indicator dye (e.g., phenol red) to change color. As a result, growth may be observed as the conversion of the support medium from a clear red to yellow color, for example, to a turbid yellow condition. Although these processes are slow, they represent compelling evidence of life and are generally accepted as the benchmark by the various sterility assurance regulatory bodies. By indirectly measuring viability as a function of the activity of a target/reporter enzyme (e.g., alpha glucosidase), it is possible to shorten the time required to get an indication of sterility. However, as indicated above, this process may still require grow out as the ultimate confirmation. Because growth and the accumulation of metabolic waste products are the end result of life processes, they may require significant time (24 to 72 hours) to become apparent With the present invention, a reporter gene (e.g., lacZ) suitable for producing an indicator enzyme (e.g., β-galactosidase) may be taken up by a test organism (e.g., a bacterial microorganism) using a suitable vehicle (e.g., plasmid or virus). In contradistinction to the prior art, in the present invention, no repressor gene is included in the test organism, and since no repressor is used, there is no need for an inducer to overcome the effects of the reporter gene. Thus, the present invention avoids the possible obfuscation of the detectable signs of life following the sterilization, and since there is no repression of expression of the reporter gene, it is possible to obtain confirmation of either the efficacy of the sterilization or the failure thereof at an earlier point in time. What is exposed to the sterilization process are the various and vital mechanisms the test organism uses to survive and grow and which are also used for the production of the indicator enzyme. These may include the DNA polymerases used for cellular growth (and replication of the plasmid), RNA polymerases for transcription of the metabolic requirements of the test organisms (and the plasmid or virus borne reporter gene, e.g., lacZ) and the ribosomal polysomes required for the translation of cellular proteins (as well as the expression of the indicator enzyme). Because the indicator enzyme may be fast acting as a signal generating mechanism, the presence of any remaining viable organisms may become apparent earlier than if they were tied to the accumulated end results of the vital growth mechanisms of the test organism.

The test organism may comprise any organism whose resistance to the intended sterilization process exceeds that of the other organisms that are to be destroyed by the sterilization process. The type of test organism used may be dependent upon a variety of factors exemplified by, but not limited to, the type of sterilization process being used. The test organism may be a microorganism. The strains that may be used may be those that are the most resistant to the process used for sterilization. The test organism may comprise one or more bacteria, pathogens, gram negative organisms, gram positive organisms, vegetative organisms, viruses, non self-replicating agents, sub-cellular components or products of cells, and/or prions. The bacterial microorganisms may be those which form endospores, i.e., bacterial spores. The test organism may comprise bacteria of the *Bacillus, Geobacillus* or *Clostridia* genera. These may include *Geobacillus stearothermophilus, Bacillus atrophaeus, Bacillus subtilis, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans, Escherichia coli*, and the like. The two most commonly used test organisms are *Geobacillus stearothermophilus* and *Bacillus atrophaeus*, most often and preferably in the form of spores. As known in the art, *Geobacillus stearothermophilus* may also be known as *Bacillus stearothermophilus*.

The test organism may further comprise fungi, mycobacteria, protozoa, vegetative bacteria, and the like. Examples of fungi that may be used may include *Aspergillus niger, Candida albicans, Trichophyton mentagrophytes, Wangiella dermatitis*, and the like. Examples of mycobacteria that may be used may include *Mycobacterium chelonae, Mycobacterium gordonae, Mycobacterium smegmantis, Mycobacterium terrae, Mycobacterium bovis, Mycobacterium tuberculosis*, and the like. Examples of protozoa that may be used may include *Giardia lamblia, Cryptosporidium parvum*, and the like. Examples of vegetative bacteria that may be used may include *Aeromonas hydrophila, Enterococcus faecalis, Streptococcus faecalis, Enterococcus faecium, Streptococcus pyrogenes, Escherichia coli, Klebsiella pneumoniae, Legionella pneumophila, Methylobacterium, Pseudomonas aeruginosa, Salmonella choleraesuis, Helicobacter pylori, Micrococcus radiodurans, Deinococcus radiodurans, Staphylococcus aureus, Staphylococcus epidermidis, Stenotrophomonas maltophilia*, and the like. Organisms such as *Geobacillus stearothermophilus, Bacillus atrophaeus, Bacillus subtilis, Bacillus coagulans, Clostridium sporogenes*, and the like, may be used for determining the efficacy of moist heat sterilization (autoclaving), with *Geobacillus stearothermophilus* being especially useful.

Vegetative organisms such as vegetative bacteria, vegetative cells and/or their constituent parts may be used as the test organism. Examples may include the coliform species and cells that do not form endospores e.g., *Aeromonas hydrophila*, *Enterococcus faecalis*, *Streptococcus faecalis*, *Enterococcus faecium*, *Streptococcus pyrogenes*, *Escherichia coli*, *Klebsiella* (*pneumoniae*), *Legionella pneumophila*, *Methylobacterium*, *Pseudomonas aeruginosa*, *Salmonella choleraesuis*, *Helicobacter pylori*, *Staphylococcus aureus*, *Staphylococcus epidermidis*, *Stenotrophomonas maltophilia*, and the like.

These test organisms may be used in combination with one or more excipients. Excipients may be defined as a broad class of generally inert compounds that may be used to stabilize labile entities. A subclass of excipients that may be used includes the carbohydrates, for example, oligomeric and polymeric saccharides. An example of such a compound may be trehalose which is a disaccharide. High concentrations of trehalose in the tissues of certain organisms may allow the organisms to survive in a state of water deficiency. Trehalose may be used to revive functional cellular components after dehydration. Trehalose may provide stability to membranes and other macromolecular structures essential to the viability of a cell under extreme environmental conditions (e.g., freeze drying). Other stabilizing excipient compounds may include simple sugars (e.g. sucrose, glucose, maltose, and the like) and long chain polymers (e.g. dextrans, starch, agarose, cellulose, and the like). Other non-carbohydrate based excipients may include proteins, phosphonates, buffering agents, waxes, lipids, oils as well as other hydrocarbon based materials.

The test organisms may comprise one or more non-self-replicating agents and/or sub-cellular components or products of cells. These may be used because of their clinical significance or because of their use as agents of bioterrorism. These indicator materials may comprise cellular strains which may now have resistance to normal means of antibiotic treatment or chemical disinfection due to natural or man-made modifications. Examples of the former type may include VREs (Vancomycin Resistant *enterococci*), MSRAs (Methicillin Resistant *Staphylococcus aureus*), *Mycobacterium cheloni*, and the like. These may be used because the VREs and MRSAs have developed resistance to therapeutic countermeasures (e.g., antibiotic resistance) and *M. cheloni* has developed resistance to some modes of disinfection (e.g., glutaraldehyde resistance).

The test organism may comprise one or more emerging organisms. These may represent a special risk or challenge to therapeutic course of action or disinfection. Examples of these indicator materials may include prions. Prions are not living organisms, per se, but their function as disease causing agents may be related to their structure and this structure/function relationship may be employed to determine their relative infectivity. Other non-autonomous agents (e.g. viruses) as well as sub-cellular elements and proteinaceous prions may be used.

The reporter gene that is taken up by the test organism is provided for the purpose of producing the indicator enzyme and may comprise lacZ, bgaB, xylE, cat or a mixture of two or more thereof. The term "lacZ" refers to a gene coding for β-galactosidase. The term "bgaB" refers to the gene coding for thermostable β-galactosidase from *G. stearothermophilus*. The term "xylE" refers to gene coding for catechol-2,3-dioxygenase from *Pseudomouas putida*. The term "cat" refers to the gene coding for chloramphenicol acetyltransferase, e.g., from pC194. The term "pC194" refers to a particular plasmid construct. The foregoing discussion of the reporter genes applies to other organisms, including in particular *Bacillus atrophaeus*.

The vehicle for inserting (or transfecting) the reporter gene into the test organism may comprise one or more plasmids and/or one or more viruses. These vehicles may be referred to as vectors. The plasmids may comprise circular double-stranded DNA that are separate from chromosomal DNA. The plasmids may be linear. The size of the plasmids may be in the range from about 2000 to about 20000 base pairs (bp), and in one embodiment in the range from about 5000 to about 12000 bp. One or more copies (for example, from 1 to about 3000 copies, and in one embodiment from 1 to about 60 copies, and in one embodiment from about 20 to about 3000 copies) of the same plasmid may be taken up by a single cell of the test organism. The plasmids may contain one or more DNA sequences that serve as an origin of replication. The plasmids may contain one or more genetic markers. The plasmids may contain a polylinker or a multiple cloning site (MCS) which may be a relatively short region containing one or more restriction sites allowing the insertion of DNA fragments. The plasmids may contain one or more genes that provide a selective marker to induce the test organism to retain the plasmid. The selective marker may comprise an antibiotic resistance gene and/or or a gene with nutritional capability. The plasmids may comprise conjugative plasmids which contain tra-genes (transfer operon) which may perform the process of conjugation, the non-sexual transfer of plasmids to another bacterium.

The plasmids may comprise at least one origin of replication, at least one selectable marker, at least one inducible promoter, and at least one reporter gene. The selectable marker may comprise an antibiotic resistance gene and/or a gene with exogenous nutritional capability. These may include chloramphenicol, ampicillin or spectinomycin antibiotic genes, and/or xylose or lactose nutritional genes. The inducible promoter may comprise PxylA. The term PxylA refers to a transcription promoter that in the presence of an active xylR regulator function requires xylose to remain active. The reporter gene may comprise lacZ, bgaB, xylE, cat and the like. The plasmid may comprise two origins of replication. One of the origins of replication may comprise a gram negative origin of replication and the other origin of replication may comprise a gram positive origin of replication. The gram negative origin of replication may comprise *Escherichia coli*. The gram positive origin of replication may comprise *Bacillus subtilis*, *Geobacillus stearothermophilus* or *Bacillus atrophaeus*. The plasmids may contain from about 2000 to about 20000 bp, and in one embodiment from about 5000 to about 12000 bp.

Naturally occurring plasmids exist over a broad range of host organisms in nature. They may comprise genes, regulatory elements and/or structural pieces of DNA. Plasmids usually provide some advantage to their host organism (e.g., antibiotic resistance or the ability to use certain nutritional sources of energy) and may be tolerated by their host organisms for as long as this advantageous relationship may exist. Genetically engineered plasmids may comprise a patchwork of genes, regulatory elements and/or structural pieces of interest. Since there are so many naturally occurring (and previously engineered) plasmids available, there is a wide choice of genes to choose from. For example, the genes employed may be selected based on the desired properties of the finished construct. These properties may include the ability to transform the full range of useful host organisms, provide some selective advantage to the host organism (e.g., antibiotic resistance), produce a thermostable and rapidly detectable signal on demand, and provide for the signal to be off until it is desired to turn it on. This may be accomplished by piecing together (ligation) the required attributes in the form of DNA segments from a variety of source plasmids. For example, the fragments may comprise origins of replication for both gram positive and gram negative organisms, a cat gene for chloramphenicol resistance, a bgaB gene for thermostable β-galactosidase, and an optional xylR regulator to regulate the bgaB gene product until needed.

A plasmid of specific design may be constructed by assembling the desired genetic elements. The genetic elements may be assembled by restriction digest of the desired genetic sequence from a donor plasmid or organism to produce ends of the DNA which may then be readily ligated to another genetic sequence. Typically, a 5' or 3' overhang may be produced via restriction digest on both sequences targeted for ligation. Following digestion, the target sequences may be purified and then ligated together with an enzyme (ligase). The plasmid may be constructed by assembling a base plasmid containing the origins of replication for both gram positive and gram negative organisms as well as the cat gene for chloramphenicol resistance. Following confirmation of the proper attachment of the cat gene to the base segment, the process may be repeated for both the bgaB gene segment and the terminators T1 and T2 for this gene. Upon complete assembly of the genetic elements and confirmation of proper assembly and orientation, the plasmid may be inserted into a host organism which may be used as the test organism.

A complete virus particle, which may be referred to as a virion, may be a gene transporter that may comprise nucleic acid surrounded by a protective coat of protein which may be referred to as a capsid. A capsid may comprise proteins encoded by the viral genome and its shape may serve as a basis for morphological distinction. Virally coded protein units, which may be referred to as promoters, may self-assemble to form the capsid, requiring no input from the virus genome; however, a few viruses may code for proteins which may assist the construction of their capsid. Proteins associated with nucleic acid may be more technically known as nucleoproteins, and the association of viral capsid proteins with viral nucleic acid may be referred to as a nucleocapsid. The viruses may not be considered to be living organisms and may lack the means for self-reproduction outside a host cell. The viruses used herein with bacteria may be referred to as bacteriophages or phages. Examples of the viruses may include lambda or M13 bacteriophages. The reporter gene may be inserted in the virus by first cleaving the non-recombinant phage DNA with an endonuclease and then ligating a piece of DNA to the two newly formed ends.

The vehicle (i.e., plasmid, virus) may be taken up by the test organism by: transformation or conjugation, for example, with plasmids, or transduction or transfection, for example, with viruses.

The indicator enzymes, which may be produced by the reporter gene, may comprise beta-D-galactosidase, beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof. Thermostable or thermolabile counterparts of these may be used depending upon the preferred incubation conditions for the selected host organism.

The genetically engineered biological indicator may be exposed to the sterilization medium during a sterilization process using any suitable procedure.

The sterilization indicator containing the disclosed biological indicator may be used in any process wherein the sterilization indicator is exposed to a sterilization medium during a sterilization process and then to an enzyme substrate to determine whether the sterilization process is effective. The sterilization process may employ gaseous or liquid sterilants, dry heat, radiation, and the like. The sterilization indicator along with the articles to be sterilized may be exposed to a sterilization medium during the sterilization process. Upon completion of the sterilization process, the genetically engineered biological indicator is combined with a recovery or incubation medium comprising at least one enzyme substrate. The genetically engineered biological indicator may then be incubated with the enzyme substrate for a desired period of time and examined to determine whether the sterilization process was effective.

The genetically engineered biological indicator may be used in a self-contained sterilization indicator comprising a container with two separate compartments. One of the compartments may contain the biological indicator. The other compartment may contain a recovery medium comprising the at least one enzyme substrate. In use, the sterilization indicator and the articles to be sterilized may be exposed to the sterilization medium. Following sterilization, the sterilization indicator may be activated so that the genetically engineered biological indicator comes into contact with the recovery medium sufficiently to determine whether the sterilization process was effective. These sterilization indicators may be used with any sterilization process wherein the biological indicator may be exposed to the sterilization medium, for example, sterilization processes employing gaseous sterilants.

Figure 1:
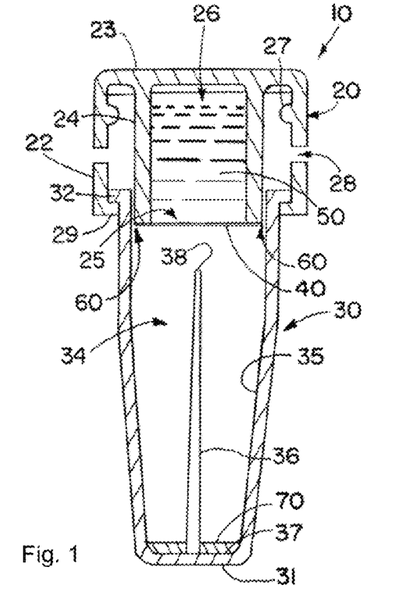
FIG. 1 is a schematic cross-sectional view of a first embodiment of a sterilization indicator suitable for use with embodiments of the present invention, in a pre-activated configuration.
Figure 2:
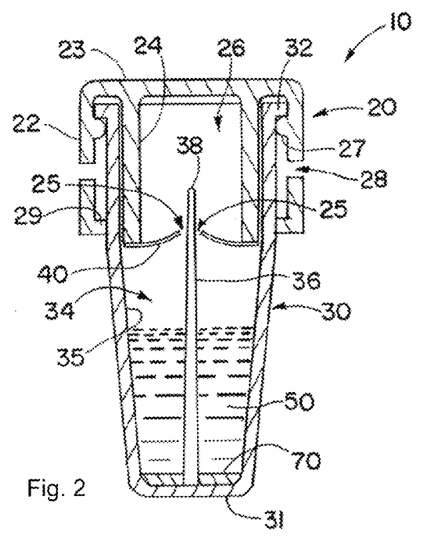
FIG. 2 is a schematic cross-sectional view of the sterilization indicator of FIG. 1 in an activated configuration.

Referring now to the drawings, FIGS. 1 and 2 show a sterilization indicator system 10 in accordance with a first exemplary embodiment of the present invention. The indicator system 10 comprises a cap 20 that is mountable on a container 30. The container 30 includes a closed, bottom end 31 and an open, upper end, and defines an interior space 34. The cap 20 has an outer wall 22, an open, lower end, and a closed, upper end 23. The cap also includes an inner wall (or walls) 24 disposed interior of the cap's outer wall, forming a separate wall, and defining an inner chamber 26. The inner chamber 26 includes an opening 25 adjacent to the bottom end of the wall(s) 24. The chamber 26 contains a fluid 50, and the cap 20 includes a breakable barrier 40 disposed about the opening 25 of the chamber 26 to encapsulate the fluid 50 within the chamber 26.

In the embodiment illustrated in FIGS. 1 and 2, the indicator system is configured for the cap 20 to be mounted to the container 30 in a snap-fit relationship. In other embodiments, not shown, the indicator system may be configured for the cap to be mounted to the container in a threaded relationship in which the cap is engaged with the container by threads and the system is activated by rotating the cap with respect to the container, i.e., screwing the cap further onto the container. As shown in FIGS. 1 and 2, the container 30 includes an annular projection 32 forming a ridge or lip adjacent or near the upper end of the container. The cap 20 includes an annular projection 29 forming a ridge or lip adjacent the bottom of the cap. The cap 20 may be mounted onto the container 30 by sliding the ridge 29 of the cap over the ridge 32 of the container. The ridge 32 of the container 30 engages the ridge 29 on the cap 20 to prevent the cap 20 and container 30 from decoupling. The cap 20 and container 30 may be sized such that the ridge 32 exerts a sufficient amount of pressure against the cap 20 to prevent the cap 20 from sliding downward without applying an external downward force to the cap 20. In this way, the breakable barrier 40 may be kept spaced apart from the edges 38 of puncture members 36 so the breakable barrier 40 does not contact and/or is not broken by the puncture members until such time as desired to activate the indicator.

As shown in FIGS. 1 and 2, the container 30 is adapted to break the breakable barrier 40. The containers include one or more projections 36 (which may also be referred to herein as "puncture members") having an edge 38 adapted to break or puncture the breakable barrier 40 when the cap 20 with the breakable barrier 40 is moved downward toward and the barrier 40 contacts the edge 38 of projection 36. The puncture member 36 is shown as being integral with and extending up from the inner, bottom wall 37 of the container. In another embodiment, not shown, puncture members 36 may extend both from the side wall 35 and from the inner, bottom wall 37.

To evaluate a sterilization process, a calibrated concentration of microorganisms is disposed within the interior 34 of the container 30. The microorganisms may be disposed directly on the walls 35 of the container or may be provided on a support member (e.g., support member 70) that is disposed within the container 30. In another embodiment the microorganisms mat be disposed directly to the bottom wall 37 The sterilization indicator is then assembled by mounting the recovery medium-filled cap 20 on the container 30. The cap 20 may be mounted by snap-fitting the cap 20 onto the container 30 as described above, or, for example, by a threaded mounting. With reference to FIG. 1, the recovery medium-filled cap 20 is mounted on the container 30 in a first, non-activated (or open) position such that the breakable barrier 40 remains intact and is not punctured by the puncture members 36. Desirably, in the first, non-activated position, the breakable barrier 40 is positioned away from and does not contact the edges 38 of the puncture members 36.

With the indicator 10 being assembled such as shown in FIG. 1, the sterilization indicator then can be subjected to a sterilization process. The cap 20 is shown as having apertures 28 through which a sterilant vapor may enter and flow into indicator system. The sterilant enters the cap through the apertures 28 (into the space between the outer wall 22 and the inner wall 24) and flows into the container 30 through a space 60 defined between the exterior surface of the inner wall 24 on the cap 20 and the inner surface of the wall 35 on the container 30. The sterilant vapor flows into the container 30 and acts upon the microorganisms of the genetically engineered biological indicator.

After the sterilization process is completed, the sterilization indicator may be activated by moving the cap 20 downward toward the container 30 to a second (or closed or activated) position, which is illustrated in FIG. 2. The cap 20 is moved downward by applying a sufficient downward force or pressure on the cap 20. As the cap 20 is moved downward, the breakable barrier 40 is brought into contact with the edge 38 of the puncture member 36, and eventually moved into a position such that the edge 38 of the puncture member 36 punctures or penetrates the breakable barrier 40. When the breakable barrier 40 is punctured, the opening 25 of the chamber 26 is exposed, and the liquid recovery medium 50 drains into the interior region 34 of the container 30 and into contact with the microorganisms as shown in FIG. 2. It may be desirable to move the cap 20 downward with a twisting motion to effect a greater or maximum opening of the breakable barrier 40 to ensure complete drainage of the growth medium into the container.

As shown in FIGS. 1 and 2, in this embodiment, the inner surface of the cap 20 includes a second annular projection 27, and the cap may be moved downward to a position such that the upper portion of the projection 27 engages the bottom of ridge 32 on the container 30, and the cap 20 is held in the second, closed/activated position. The second, closed/activated position may serve to hold the cap 20 in a sealed relationship with the container 30, which may prevent additional microorganisms from entering the system. The sterilization indicator 10 is then incubated for a sufficient period of time to allow microorganism viability to be determined. During incubation, any viable microorganisms will metabolize and grow, and this metabolism and growth releases byproducts into the culture medium. The byproducts may be detected by any selected property including, for example, pH change, color change, opacity, fluorescence, and the like.

It will be appreciated that, in another embodiment, the cap 20 does not include the second projection 27 to maintain the container in the closed position. In one alternative embodiment, the container 30 may include another annular projection or a set of detents (not shown) on the outside of the container 30 and located below the ridge 32, which projection or detents may be adapted to engage the ridge 29 on the cap to maintain the container 30 in a closed position. U.S. Pat. No. 5,770,393 illustrates such a configuration, and this patent is incorporated herein by reference for its teachings relating to configurations of cap and container. In another alternative embodiment, the inner surface of the cap 20 and the outer surface of the container 30 may be threaded, and the cap 20 may be moved into and maintained in a closed position by screwing the cap 20 onto the container 30, in which the cap 20 may be threaded as shown, e.g., in U.S. Pat. No. 8,173,388 B2, which may be consulted for additional details on this embodiment of the vial, and which is hereby incorporated herein by reference for its teachings relating to the vial and cap configuration of this and the foregoing embodiments. All of these alternative configurations are within the scope of the present invention.

As described above, the cap 20 in the embodiment illustrated in FIGS. 1 and 2 is shown as having the aperture 28 to allow for the ingress of the vapor sterilant into the indicator. It will be appreciated, however, that the cap need not be provided with such a feature. The number, size, shape, and/or location of the aperture(s) may be selected as desired, with consideration of the particular sterilant with which the sterilization indicator is to be used. For example, the location, shape, and size of the apertures in the cap and/or the container may be selected to provide a tortuous path for the entrance and exit of the sterilization vapor between the microorganisms and the surrounding environments. The tortuous path may also serve to inhibit or prevent contamination from external agents, and to make certain that an adequate amount of sterilant is available. By including the tortuous path, it is more likely that the entire load will be exposed to the sterilant thereby killing any extant microorganisms before the test organism in the sterilization indicator is killed.

Apertures may be provided in the container in addition to or as an alternative to providing apertures in the cap. Additionally, if apertures are provided in the container, they should be located such that the growth medium does not leak or spill out through such apertures when the indicator is activated and the barrier is broken.

Figure 3:
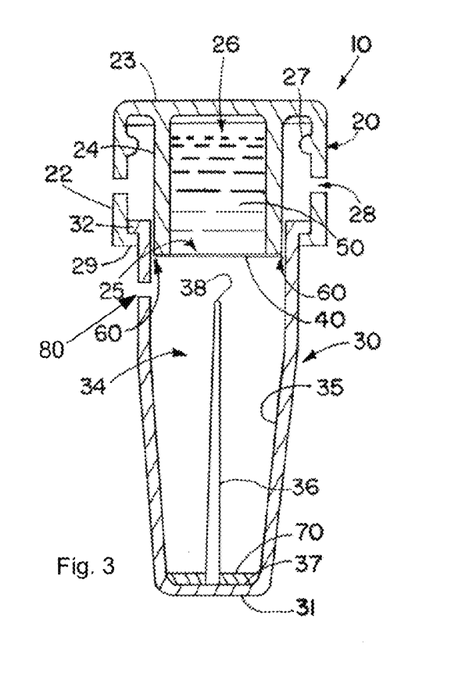
FIG. 3 is a schematic cross-sectional view of a second embodiment of a sterilization indicator suitable for use with embodiments of the present invention, in pre-activated configuration, similar to that of FIG. 1.

FIG. 3 depicts an indicator 10 in which an aperture 80 is formed in the sidewall 35 of the container 30 at an appropriate position, in addition to the apertures 28 in the cap 20. The aperture shown in FIG. 3 is in the sidewall 35 of the container 30 near the top of the container 30, in the vicinity of the edge 38 of the puncture member 36, to avoid leakage or spilling after activation. As can be seen from FIG. 3, after activation, the aperture 80 at this location will be covered by the cap 20 in the activated position. It is noted that the indicator 10 shown in FIG. 3 includes the aperture 28 in the cap 20, but this is not necessary. In one embodiment (not shown), the container 30 includes the aperture 80 and is used with a cap similar to the cap 20, but which does not include an aperture such as the aperture 28. Thus, an aperture can be provided either in the cap or in the container, or in both the cap and the container.

After the sterilization process has been completed, the cap 20 is pressed or twisted downward such that the edge 38 of the puncture member 36 penetrates and breaks the breakable barrier 40 releasing the growth medium in the space 26 to mix with and incubate with any of the genetically engineered biological indicator microorganisms that may have survived the sterilization process. The recovery medium 50 may comprise an aqueous medium or aqueous solution that provides for germination, metabolism and subsequent grow out of organisms as required. The aqueous medium or aqueous solution may be buffered. The indicator enzyme, if present as a result of having been produced by the reporter gene in any surviving genetically engineered biological indicator microorganisms, contacts the enzyme substrate resulting in the formation of the enzyme-modified product which has a detectable color or fluorescence or other characteristic, such as pH change.

The enzyme substrate may comprise a substance or mixture of substances which when acted upon by the indicator enzyme is converted into an enzyme-modified product. In general, the enzyme-modified product may comprise a luminescent, fluorescent, or colored material. Alternatively, the enzyme substrate may comprise one or more compounds which when acted upon by the enzyme, may yield a product (e.g., a reactive intermediate or a substance capable of changing the pH of the medium) which reacts with an additional compound or composition to yield a luminescent, fluorescent, or colored material.

There are two basic types of enzyme substrates that may be used for the detection of specific indicator enzymes. The first type of enzyme substrate may be either fluorogenic or chromogenic, and may be given a general chemical formula such as, AB. When acted upon by the indicator enzyme, AB, may break down to A+B. B, for example, may be either fluorescent or colored. In one embodiment, two B compounds may react together to produce the fluorescent or colored signal. A specific example of a fluorogenic substrate of this type may be 4-methylumbelliferyl phosphate. In the presence of the indicator enzyme phosphatase, the substrate may be broken down into 4-methylumbelliferone and phosphate. Other fluorogenic substrates of this type may include the derivatives of 4-methylumbelliferyl, 7-amido-4-methylcoumarin, indoxyl and fluorescein. An example of a chromogenic substrate of this type may be 5-bromo-4-chloro-3-indolyl phosphate. In the presence of phosphatase, the substrate may be broken down into indigo blue and phosphate. Other chromogenic substrates of this type may include derivatives of 5-bromo-4-chloro-3-indolyl, nitrophenol and phenolphthalein.

The second type of enzyme substrate may be given by a general chemical formula CD, for example, which may be converted by a specific enzyme to C+D. However, neither C nor D may be fluorescent or colored, but D may be capable of being further reacted with compound Z to give a fluorescent or colored compound, thus indicating enzyme activity. A specific fluorogenic example of this type may be the amino acid lysine. In the presence of the enzyme lysine decarboxylase, lysine may lose a molecule of $CO_2$. The remaining part of the lysine may then be called cadaverine, which is strongly basic. A basic indicator such as 4-methylumbelliferone may be incorporated and may be fluoresce in the presence of a strong base. A chromogenic substrate of this type may be 2-naphthyl phosphate. The indicator enzyme phosphatase, may react with the enzyme substrate to yield beta-naphthol. The liberated beta-naphthol may react with a chromogenic reagent containing 1-diazo-4-benzoylamino-2,5-diethoxybenzene to produce a violet color.

The enzyme substrate may comprise a fluorogenic compound, defined herein as a compound capable of being enzymatically modified, e.g., by hydrolysis, to provide a derivative fluorophor which has an appreciably modified or increased fluorescence.

The fluorogenic compounds may in themselves be either non-fluorescent or meta-fluorescent (i.e., fluorescent in a distinctly different way, e.g., either by color or intensity, than the corresponding enzyme-modified products) and appropriate wavelengths of excitation and detection, may be used to separate the fluorescence signal developed by the enzyme modification from any other fluorescence that may be present.

A number of enzyme substrates for indicator enzymes of diverse origins may be used. These may include fluorogenic 4-methylumbelliferyl derivatives (hydrolyzable to 4-methylumbelliferone); derivatives of 7-amido-4-methyl-coumarin; diacetylfluorescein derivatives; and fluorescamine.

Derivatives of 4-methylumbelliferyl that may be used as the enzyme substrate may include: 4-methylumbelliferyl-2-acetamido-4,6-O-benzylidene-2-deoxy-beta-D-lucopyranoside; 4-methylumbelliferyl acetate; 4-methylumbelliferyl-N-acetyl-beta-D-galactosaminide; 4-methylumbelliferyl-N-acetyl-alpha-D-glucosaminide; 4-methylumbelliferyl-N-acetyl-beta-D-glucosaminide; 2'-(4-methylumbelliferyl)-alpha-D-N-acetyl neuraminic acid; 4-methylumbelliferyl-alpha-L-arabinofuranoside; 4-methylumbelliferyl alpha-L-arabinoside; 4-methylumbelliferyl butyrate; 4-methylumbelliferyl-beta-D-cellobioside; methylumbelliferyl-beta-D-N,N'-diacetyl chitobioside; 4-methylumbelliferyl elaidate; 4-methylumbelliferyl-beta-D-fucoside; 4-methylumbelliferyl-alpha-L-fucoside; 4-methylumbelliferyl-beta-L-fucoside; 4-methylumbelliferyl-alpha-D-galactoside; 4-methylumbelliferyl-beta-D-galactoside; 4-trifluoromethylumbelliferyl beta-D-galactoside; 6,8-difluoro-4-methylumbelliferyl-beta-D-galactoside; 4-methylumbelliferyl-alpha-D-glucoside; 4-methylumbelliferyl-beta-D-glucoside; 4-methylumbelliferyl-7,6-sulfo-2-acetamido-2-deoxy-beta-D-glucoside; 4-methylumbelliferyl-beta-D-glucuronide; 6,8-difluoro-4-methylumbelliferyl-beta-D-glucuronide; 4-methylumbelliferyl p-guanidinobenzoate; 4-methylumbelliferyl heptanoate; 4-methylumbelliferyl-alpha-D-mannopyranoside; 4-methylumbelliferyl-beta-D-mannopyranoside; 4-methylumbelliferyl oleate; 4-trifluoromethylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl-beta-D-N,N',N''-triacetylchitotriose; 4'-methylumbelliferyl 2,3,5-tri-beta-benzoyl-alpha-L-arabinofuranoside; 4-methylumbelliferyl-beta-trimethylammonium cinnamate chloride; 4-methylumbelliferyl 4-guanidinobenzoate; and 4-methylumbelliferyl-beta-D-xyloside.

Derivatives of 7-amido-4-methylcoumarin that may be used as the enzyme substrate may include: L-alanine-7-amido-4-methylcoumarin; L-proline-7-amido-4-methylcoumarin; L-tyrosine-7-amido-4-methylcoumarin; L-arginine-7-amido-4-methylcoumarin; L-citrulline-7-amido-4-methylcoumarin; L-leucine-7-amido-4-methylcoumarin; L-methionine-7-amido-4-methylcoumarin; L-pyroglutamic acid 7-amido-4-methylcoumarin; L-aspartic acid beta-(7-amido-4-methylcoumarin); L-glutamic acid 1-(7-amido-4- methylcoumarin); L-phenylalanine-7-amido-4-methylcoumarin; and 7-glutaryl-phenylalanine-7-amido-4-methylcoumarin.

Peptide derivatives of 7-amido-4-methyl coumarin that may be used as the enzyme substrate may include: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methylcoumarin; N-succinyl-Leu-Tyr-7-amido-4-methylcoumarin; Gly-Pro 7-amido-4-methylcoumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Derivatives of diacetylfluorescein that may be used as the enzyme substrate may include fluorescein diacetate, fluorescein dibutyrate, 2',7'-dichlorofluorescein diacetate, fluorescein di-(beta-D-N-acetygalactosamine), fluorescein di-(beta-D-galactoside), fluorescein mono-(beta-D-galactoside), and fluorescein dilaurate.

Where the indicator enzyme whose activity is to be detected is alpha-D-glucosidase, chymotrypsin or fatty acid esterase, a fluorogenic enzyme substrate that may be used may be 4-methylumbelliferyl-alpha-D-glucoside, 7-glutarylphenylalanine-7-amido-4-methyl coumarin, or 4-methylumbelliferyl heptanoate, respectively. Where the indicator enzyme whose activity is to be detected is alpha-L-arabinofuranosidase, a fluorogenic enzyme substrate that may be used may be 4-methylumbelliferyl-alpha-L-arabinofuranoside. Where the indicator enzyme whose activity is to be detected is beta-D-glucosidase, a fluorogenic enzyme substrate that may be used may be 4-methylumbelliferyl-beta-D-glucoside.

An enzyme substrate that may be used may be a chromogenic compound capable of being enzymatically modified to give a derivative chromophor, or a product which reacts with another compound to give a derivative chromophor, which chromophor has a different or more intense color. The chromogenic compounds may be non-colored or colored in a distinctly different way, e.g., either by color or intensity, than the corresponding enzyme-modified products. Appropriate wavelengths of excitation and detection, in manners well known to users of colorometric instrumentation, may be used to separate the colored signal developed by the enzyme modification from any other color that may be present.

Chromogenic compounds that may be used as enzyme substrates may include 5-bromo-4-chloro-3-indolyl derivatives; nitrophenyl derivatives; indoxyl derivatives; and phenolphthalein derivatives.

Derivatives of 5-bromo-4-chloro-3-indolyl that may be used may include 5-bromo-6-chloro-3-indolyl acetate, 5-bromo-4-chloro-3-indolyl acetate, 5-bromo-4-chloro-3-indoxyl-beta-D-galactopyranoside, 5-bromo-4-chloro-3-indolyl-1,3-diacetate, 5-bromo-4-chloro-3-indolyl-beta-D-fucopyranoside, 5-bromo-4-chloro-3-indolyl-beta-D-glucopyranoside, 5-bromo-4-chloro-3-indolyl-beta-D-glucuronic acid, 5-bromo-4-chloro-3-indolyl phosphate, and 5-bromo-4-chloro-3-indolyl sulfate.

Derivatives of nitrophenyl that may be used may include p-nitrophenol and o-nitrophenol derivatives. These include diethyl-p-nitrophenyl phosphate; di-p-nitrophenyl phosphate; p-nitrophenyl-2-acetamido-2-deoxy-3-O-beta-galactopyranosyl-beta-glucopyranoside; p-nitrophenyl-2-acetamido-2-deoxy-beta-glucopyranoside; p-nitrophenyl acetate; p-nitrophenyl-N-acetyl-beta-D-glucosaminide; p-nitrophenyl-beta-D-N,N'-diacetylchitobioside; p-nitrophenyl-alpha-glucopyranoside; p-nitrophenyl-alpha-maltoside; p-nitrophenyl-beta-maltoside; p-nitrophenyl-alpha-mannopyranoside; p-nitrophenyl-beta-mannopyranoside; p-nitrophenyl myristate; p-nitrophenyl palmitate; p-nitrophenyl phosphate; bis(p-nitrophenyl)phosphate; tris(p-nitrophenyl)phosphate; p-nitrophenyl-beta-glucopyranoside; p-nitrophenyl-beta-glucuronide; alpha-p-nitrophenylglycerine; p-nitrophenyl-alpha-rhamnopyranoside; p-nitrophenyl stearate; p-nitrophenyl sulfate; p-nitrophenyl-2,3,4,6-tetra-O-acetyl-beta-glucosaminide; p-nitrophenyl thymidine monophosphate; p-nitrophenyl-2,3,4-tri-O-acetyl-beta-glucuronic acid methyl ester; and p-nitrophenyl valerate.

Useful o-nitrophenols may include o-nitrophenyl acetate, o-nitrophenyl-beta-glucoside and o-nitrophenyl-beta-D-glucopyranoside. Other useful nitrophenyl derivatives may include nitrophenyl-beta-fucopyranoside; nitrophenyl-alpha-galactopyranoside; nitrophenyl-beta-galactopyranoside; nitrophenyl butyrate; nitrophenyl caprate; nitrophenyl caproate; nitrophenyl caprylate; nitrophenyl laurate; and nitrophenyl propionate.

Indoxyl derivatives that may be used may include indoxyl-acetate; indoxyl beta-D-glucoside; 3-indoxyl sulfate; and 3-indoxyl phosphate.

Phenolphthalein derivatives that may be used may include: phenolphthalein dibutyrate; phenolphthalein diphosphate; phenolphthalein disulfate; phenolphthalein glucuronic acid; phenolphthalein mono-beta-glucosiduronic acid; phenolphthalein mono-beta-glucuronic acid; and phenolphthalein mono-phosphate.

The above-described chromogenic enzyme substrates may react directly with an appropriate indicator enzyme to produce a chromophor.

Additional enzyme substrates containing 1-naphthyl, 2-naphthyl and Napthyl-AS-BI derivatives may be employed if the derivative enzyme modified product is further reacted with a chromogenic reagent, such as diazotized dyes, e.g., 1-diazo-4-benzoylamino-2,5-diethoxybenzene, 1-diazo-4-benzoylamino-2,5-diethoxybenzene, p-diazo-2,5-diethoxy-N-benzoyalanine, 4-chloro-2-methylbenzene diazonium chloride, and o-aminoazotoluene diazonium salt, to produce a chromophor.

Derivatives of 1-naphthyl that may be used may include 1-naphthyl-N-acetyl-beta-D-glucosaminide.

Derivatives of 2-naphthyl that may be used may include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine 2-naphthyl-amine; 2-naphthyl-phosphate; 6-Br-2-naphthyl-alpha-D-galacto-pyranoside; 2-naphthyl-beta-D-galacto-pyranoside; 2-naphthyl-2-D-glucopyranoside; 6-bromo-2-naphthol-beta-D-glucopyranoside; 6-bromo-2-naphthyl-2-D-mannopyranoside; and 2-naphthyl-alpha-L-fucopyranoside.

Derivatives of naphthyl-AS-BI that may be used may include naphthyl-AS-BI-phosphate; and naphthyl-AS-BI-beta-D-glucuronide.

Where the indicator enzyme whose activity is to be detected is alpha-D-glucosidase, the enzyme substrate may be p-nitrophenyl-alpha-glucopyranoside. Where the indicator enzyme whose activity is to be detected is alpha-L-arabinofuranosidase, the enzyme substrate that may be used may be p-nitrophenyl-alpha-L-arabinofuranoside. Where the indicator enzyme whose activity is to be detected is β-galactosidase, the enzyme substrate may be 5-bromo-4-chloro-3-indolyl-β-D-galactopyranoside or 4-methylumbelliferone-β-D-galactopyranoside.

The enzyme substrate that may be used may depend upon the identity of the indicator enzyme whose activity is under study. Below is a list of a number of enzyme substrates and corresponding indicator enzymes which may react with the enzyme substrate to produce a product having appreciably modified or increased fluorescence or color.

| Enzyme Substrate | Indicator Enzyme |
| --- | --- |
| 4-Methylumbelliferyl acetate | Esterase |
| 4-Methylumbelliferyl butyrate | Esterase |
| 4-Methylumbelliferyl elaidate | Lipase |
| 4-Methylumbelliferyl-β-D-galactopyranoside | β-D-Galactosidase |
| 4-Methylumbelliferyl-α-D-galactopyranoside | α-D-Galactosidase |
| 4-Methylumbelliferyl-α-D-glucopyranoside | α-D-Glucosidase |
| 4-Methylumbelliferyl-β-D-glucopyranoside | β-D-Glucosidase |
| 4-Methylumbelliferyl heptanoate | Esterase |
| 4-Methylumbelliferyl oleate | Lipase |
| 4-Methylumbelliferyl phosphate | Acid or Alkaline Phosphatase |
| 4-Methylumbelliferyl propionate | Esterase |
| 4-Methylumbelliferyl-β-D-galactoside | β-D-Galactosidase |
| 4-Methylumbelliferyl-β-D-glucoside | β-D-Glucosidase |
| 4-Methylumbelliferyl-α-D-glucoside | α-D-Glucosidase |
| 4-Methylumbelliferyl-α-L-arabinofuranoside | α-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | α-D-Galactosidase |
| p-Nitrophenyl phosphate | Alkaline or Acid phosphatase |
| p-Nitrophenyl acetate | Lipase |
| o-Nitrophenyl-β-D-galactopyranoside | β-D-Galactosidase |
| p-Nitrophenyl-α-D-galactopyranoside | α-D-Galactosidase |
| o-Nitrophenyl-β-D-glucopyranoside | β-D-Glucosidase |
| p-Nitrophenyl-α-D-glucopyranoside | α-D-Glucosidase |
| p-Nitrophenyl-β-D-glucuronide | β-D-Glucuronidase |
| p-Nitrophenyl-α-L-arabinofuranoside | α-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate di-Na salt | Alkaline Phosphatase |
| Phenolphthalein dibutyrate | Esterase |
| Phenolphthalein diphosphate | Acid or Alkaline phosphatase |
| Phenolphthalein diphosphate penta-Na salt | Acid or Alkaline phosphatase |
| Phenolphthalein-β-D-glucuronide Na salt | β-D-Glucuronidase |
| Phenolphthalein-β-D-glucuronide | β-D-Glucuronidase |
| L-Phenylalanine ethyl ester HCl | Chymotrypsin |
| Phenyl-β-D-galactopyranoside | β-D-Galactosidase |
| Phenyl-β-D-glucuronide | β-D-Glucuronidase |
| Phenyl-β-D-glucopyranoside | β-D-Glucosidase |
| Phenyl-β-D-glucuronide | β-D-Glucuronidase |
| Phenyl-α-D-glucoside | α-D-Glucosidase |
| Sodium β-glycerophosphate | Acid or Alkaline phosphatase |
| Sodium 1-naphthyl phosphate | Acid or Alkaline phosphatase |
| Sodium 2-naphthyl phosphate | Acid or Alkaline phosphatase |
| 2-Naphthyl-butyrate | Esterase |
| β-Naphthyl acetate | Lipase |
| 6-Br-2-naphthyl-β-D-glucoside | β-D-Glucosidase |
| L-Leucyl-2-naphthylamide aminopeptidase | Leucine |
| L-Valyl-2-naphthylamide aminopeptidase | Valine |
| N-glutaryl-phenylalanine-2-naphthylamine | Chymotrypsin |
| Naphthyl-AS-BI-phosphate | Phosphohydralase |
| Indoxyl acetate | Lipase |
| N-Methylindoxyl acetate | Lipase |
| N-Methylindoxyl myristate | Lipase |
| 5-Bromoindoxyl acetate | Lipase |
| 3-Indoxyl phosphate | Acid or Alkaline phosphatase |
| Indoxyl-β-D-glucoside | β-D-Glucosidase |
| 5-Br-4-Cl-3-Indolyl acetate | Lipase |
| 5-Br-4-Cl-3-Indolyl phosphate | Alkaline or Acid phosphatase |
| 5-Br-4-Cl-3-Indolyl-β-D-glucuronic acid | β-D-Glucuronidase |
| Diacetylfluorescein | Lipase/esterase |

Where the indicator enzyme is β-galactosidase, the enzyme substrate may comprise 5-Bromo-4-chloro-3-indolyl-β-D-galactopyranoside (X-gal), 5-Bromo-6-chloro-3-indolyl-β-D-galactopyranoside (Mag-gal), 5-Bromo-3-indolyl-(3-D-galactopyranoside (Bluo-gal), 6-Bromo-2-naphthyl-β-D-galactopyranoside, 6-chloro-3-indolyl-β-D-galacotpyranoside (Rose-gal), 3-Indoxyl-β-D-galactopyranoside (Y-gal), 5-Iodo-3-indoxyl-β-D-galactopyranoside, N-methylindoxyl-β-D-galactopyranoside, 2-Nitrophenyl-β-D-galactopyranoside (ONPG), 4-Nitrophenyl-β-D-galactopyranoside (PNPG), Phenyl-β-D-galactopyranoside (P-gal), 2-Chloro-4-nitrophenyl-β-D-lactoside, 4-methylumbelliferyl-β-D-galactopyranoside, 4-trifluoromethylumbelliferyl-β-D-galactopyranoside, Fluorescein di(β-D-galactopyranoside) (FDG), Fluorescein mono-(3-D-galactopyranoside, Fluorescein di-(β-D-acetyl galactosamine), 4-Methylumbelliferyl-β-D-lactopyranoside, 2-Napthyl-β-D-galactopyranoside, 8-Hydroxyquinoline-β-D-galactopyranoside, Resorufin (β-D-galactopyranoside, 3-Carboxyumbelliferyl-β-D-galactopyranoside, 4-Chloromethyl-6,8-difluoroumbelliferyl-β-D-galactopyranoside, 6,8-Difluoro-4-methylumbelliferyl-β-D-galactopyranoside, 6,8-Difluoro-4-heptadecylumbelliferyl-β-D-galactopyranoside, 5-(Pentafluorobenzoylamino)-fluorescein-β-D-galactopyranoside, $C_2$-fluorescein-β-D-galactopyranoside, $C_8$-fluorescein-β-D-galactopyranoside, $C_{12}$-fluorescein-β-D-galactopyranoside, 5-Chloromethylfluorescein-β-D-galactopyranoside, $C_{12}$-resorufin-β-D-galactopyranoside, 7-Hydroxyl-9H-(1,3-dichloro-9,9-dimethylacridin-2-one) (DDAO), or a mixture of two or more thereof.

The concentration of enzyme substrate in the aqueous solution or aqueous medium may be dependent upon the identity of the enzyme substrate and the indicator enzyme, the amount of enzyme-modified product that must be generated to be detectable, either visually or by instrument, and the amount of time required to determine whether indictor enzyme is present. The amount of enzyme substrate that may be sufficient may be the amount needed to react with any indicator enzyme that may be present after the sterilization has been completed such that an enzyme-modified product at a molar concentration of at least about $10^{-15}$ molar may be produced within a period of up to about 4 hours, and in one embodiment a molar concentration of at least about $10^{-8}$ molar within a period up to about 2 hours.

The pH of the aqueous solution aqueous medium containing the nutrient growth media and enzyme substrate may be in the range from about 5 to about 9.5, and in one embodiment about 7.5.

Here, and elsewhere in the present disclosure, the numerical limits of the range and ratio limitations can be combined. Thus, for example, in the foregoing, although not specifically enumerated, a pH in the range from about 6 to about 9, and a pH in the range from about 7 to about 8, are included within the specifically disclosed pH range. Intervening integral and fractional values are deemed to be disclosed within all ranges set forth in the present application.

The enzyme substrate in the recovery medium may be incubated with the biological indicator after the biological indicator has been subjected to the sterilization cycle. Incubation may be continued for a period of time and under conditions sufficient to liberate a detectable amount of the enzyme-modified product, assuming any of the biological indicator remains functional. In general, the amount of enzyme-modified product which may be detectable may be as low as about $1 \times 10^{-15}$ molar. The incubation conditions may be sufficient to generate at least about $1 \times 10^{-8}$ molar of enzyme-modified product, and in one embodiment from about $1 \times 10^{-6}$ to about $1 \times 10^{-5}$ molar of enzyme-modified product. The incubation time and temperature needed to produce a detectable amount of enzyme-modified product may depend upon the identity of the indicator enzyme and the enzyme substrate, and the concentrations of each present in the recovery medium. In general, the incubation temperature may be in the range from about 20° C. to about 70° C. The incubation time may be in the range up to about 4 hours, and in one embodiment in the range from about 0.01 to about 4 hours, and in one embodiment in the range from about 0.1 to about 3 hours, and in one embodiment in the range from about 0.1 to about 2 hours, and in one embodiment in the range from about 0.2 to about 1 hour, and in one embodiment, from about 1 minute to about 30 minutes.

Generally applicable methods for detecting the enzyme-modified product that may be used may include photometric, potentiometric, gravimetric, calorimetric, conductometric, or amperometric techniques. Fluorometric or spectrophotometric methods may be used. For example, the enzyme substrate may comprise a 4-methylumbelliferyl derivative which on interaction with the indicator enzyme may give rise to umbelliferone which may be monitored fluorometrically, or the substrate may comprise a nitrophenol, or similar type of derivative, which on interaction with the indicator enzyme may give rise to an enzyme-modified product which may be monitored colorimetrically.

The biological indicator, although herein described primarily in terms of a single indicator enzyme, may provide a plurality of indicator enzymes. For example, the biological indicator may provide three types of indicator enzymes, one enzyme being resistant to heat, a second being resistant to gaseous sterilizing media, and a third being resistant to radiation, e.g., gamma or beta irradiation.

Advantages of using the disclosed genetically engineered biological indicator may include providing results of whether the sterilization is effective within a relatively short period of time as described above for the incubation period, since the desired result will generally become apparent within the incubation period, if at all. By virtue of the use of the disclosed genetically engineered biological indicator, it may be possible to measure the viability of a test organism directly, rather than by indirect measurement of a surrogate molecule. The use of the disclosed biological indicator may not be limited to any particular method of sterilization. That is, the disclosed biological indicators may be used for any sterilization process. The effectiveness of a sterilization process may be determined using the disclosed genetically engineered biological indicator without requiring grow out to provide final confirmation of the effectiveness of the sterilization. By using the disclosed biological indicator, it may not be necessary to employ an electrochemical sensor to determine whether the sterilization is effective, although more rapid results with a sensor may be possible. The disclosed biological indicator may be amendable to use with instant read applications such as chip or sensor applications. The disclosed genetically engineered biological indicator may be applicable to any process employing a most resistant organism, clinically significant organism or bio-warfare organism.

The use of the disclosed genetically engineered biological indicator for detecting the effectiveness of a sterilization process may involve the use of measurement based on a genetic theory model (only a living cell can express a gene). The disclosed genetically engineered biological indicator may respond to any lethal event or combination of lethal events. The disclosed biological indicator may provide a fast acting response to any biocidal mode of action (steam, peracetic acid, ethylene oxide, liquid formaldehyde, gaseous formaldehyde, stabilized liquid hydrogen peroxide, vaporous hydrogen peroxide, dry heat, ozone, ortho-phthalaldehyde, glutaraldehyde, chloramines, quaternary amines, phenolics, iodophores, ionizing radiation, ultraviolet radiation, pulsed white light, plasma, microwave radiation, etc.).

A significant benefit of the present invention includes the avoidance of interference with the determination of the indicator color change, fluorescence, etc., that has been observed in conventional systems due to the breakdown of the inducer that is required when a repressor gene is included in the genetically engineered biological indicator microorganism. By removing the need for a repressor gene in the genetically engineered biological indicator microorganism, the need for any inducer is also removed, and thus the problem of discoloration due, e.g., to xylose decomposition, and problems that may arise from breakdown of other inducers, is avoided. In addition, the genetic modification is significantly simplified by omitting the need to include the repressor gene in the vector used to transfect the indicator microorganism.

EXAMPLES

Figure 4:
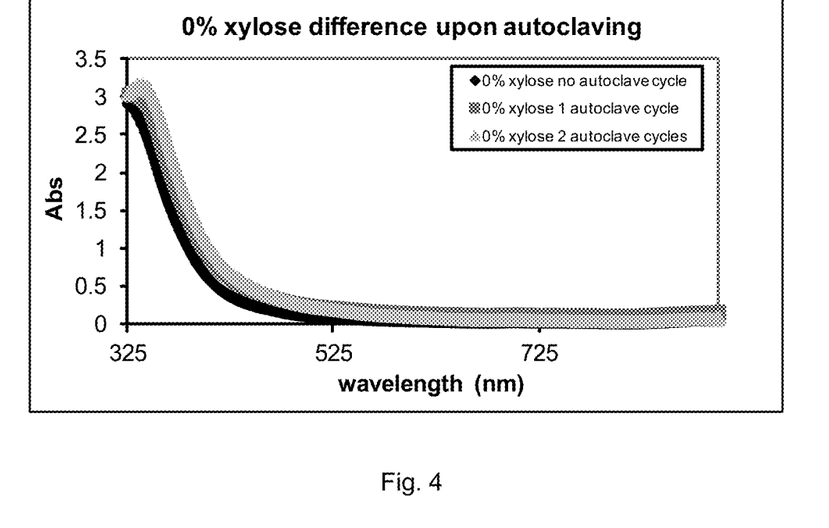
FIG. 4 is a graph showing the effects of none, one and two autoclave cycles on a recovery medium that contains no xylose.
Figure 5:
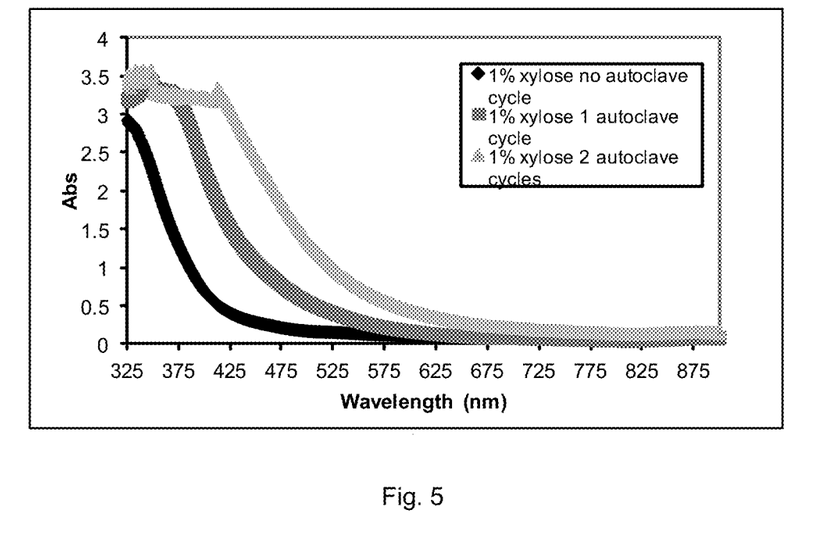
FIG. 5 is a graph showing the effects of none, one and two autoclave cycles on a recovery medium that contains 1% xylose.

The effects of the presence of xylose, and the effects of omitting xylose, and thus the benefits of the present invention, are shown by FIGS. 4 and 5, which are graphs of the absorbance of light at wavelengths ranging from 325 nm to 900 nm, before autoclaving, after one cycle of autoclaving and after two cycles of autoclaving. As will be understood, at least the second compartment, which would conventionally contain the inducer, will undergo two cycles of autoclaving before the absorbance is read in a process to determine the efficacy of a sterilization. The first autoclave cycle occurs when the sterilization indicator is being manufactured, and it is necessary to assure the sterility of the growth medium and the enzyme substrate; and the second autoclave cycle occurs when the sterilization indicator is subjected to the sterilization process for which it is the indicator.

FIG. 4 is a graph showing the absorbance of a growth medium free of xylose (i.e., containing zero percent xylose) before autoclaving, after a single cycle of autoclaving and after two cycles of autoclaving. In the example of FIG. 4, the enzyme substrate of interest absorbs electromagnetic radiation at 360 nm and emits fluorescence at 420 nm. As can be seen in the graph of FIG. 4, there is very little difference in the absorbance of the growth medium in the vicinity of 420 nm.

FIG. 5 is a graph showing the absorbance of a growth medium containing 1% xylose before autoclaving, after a single cycle of autoclaving and after two cycles of autoclaving. In the example of FIG. 5, the same enzyme substrate of interest is used, which absorbs electromagnetic radiation at 360 nm and emits fluorescence at 420 nm. As can be seen in the graph of FIG. 5, there is very little absorbance of the growth medium initially in the vicinity of 420 nm, but the absorbance of the growth medium increases dramatically after only one autoclave cycle, and the absorbance of the growth medium increases even further after the second autoclave cycle, in the vicinity of 420 nm. The absorbance of the autoclaved growth medium after one or two autoclave cycles is so great that it would be expected to at least partially and possibly fully obfuscate any color change or fluorescence resulting from growth of surviving genetically engineered biological indicator microorganisms, and thus to interfere with the determination of the efficacy of a sterilization process.

The present invention has been made in order to avoid the problem so clearly evident from the comparison of the graph of FIG. 4 with that of FIG. 5.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A sterilization indicator, comprising:
a first compartment containing a genetically engineered biological indicator, the first compartment being adapted to permit the biological indicator to be brought into contact with a sterilization medium during sterilization; and
a second compartment containing at least one enzyme substrate, the second compartment being adapted to maintain the enzyme substrate separate from the biological indicator during sterilization, and the second compartment being adapted to permit the enzyme substrate to contact the biological indicator after the biological indicator has been exposed to the sterilization medium;
wherein the genetically engineered biological indicator comprises at least one test organism and at least one reporter gene suitable for producing an indicator enzyme, the reporter gene being taken up by the test organism;
wherein the test organism in the sterilization indicator is free of any active or activatable repressor gene that would inhibit expression of the reporter gene if present in the test organism or sterilization indicator, and
wherein the indicator enzyme and the enzyme substrate are selected such that enzymatic action of the indicator enzyme upon the enzyme substrate yields a detectable signal.

2. The sterilization indicator of claim 1 wherein the reporter gene is taken up by the test organism using at least one plasmid and/or at least one virus.

3. The sterilization indicator of claim 1 or 2 wherein the test organism comprises spores of *Geobacillus stearothermophilus* and/or *Bacillus atrophaeus*.

4. The sterilization indicator of claim 1 wherein the reporter gene comprises lacZ, bgaB, xylE, cat, or a mixture of two or more thereof.

5. The sterilization indicator of claim 1 wherein the indicator enzyme comprises beta-D-galactosidase, beta-D-glucosidase, alpha-D-glucosidase, alkaline phosphatase, acid phosphatase, butyrate esterase, caprylate esterase lipase, chloroamphenicol acetytransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof.

6. The sterilization indicator of claim 1 wherein the reporter gene comprises lacZ or bgaB and the indicator enzyme comprises beta-D-galactosidase.

7. The sterilization indicator of claim 2 wherein the plasmid comprises a reporter gene and is free of any repressor gene.

8. The sterilization indicator of claim 2 wherein the virus comprises at least one gene transporter that comprises nucleic acid surrounded by a capsid, the gene transporter comprising a reporter gene and being free of any repressor gene.

9. The sterilization indicator of claim 8 wherein the virus comprises at least one bacteriophage.

10. The sterilization indicator of claim 8 wherein the virus comprises lambda or M13 bacteriophage.

11. A sterilization process, comprising:
exposing an article to be sterilized and the sterilization indicator of claim 1 to a sterilization medium;
combining contents of the first compartment and the second compartment;
incubating the combined contents of the first compartment and the second compartment; and
determining efficacy of the sterilization process by detecting the presence or absence of the detectable signal following the incubating.

12. The sterilization process of claim 11 wherein the sterilization medium comprises steam, dry heat, radiation, plasma, one or more gaseous sterilants and/or one or more liquid sterilants.

13. The sterilization process of claim 11 wherein the sterilization medium comprises electron beam radiation, electromagnetic radiation, gamma radiation, beta radiation, ethylene oxide, gaseous hydrogen peroxide, liquid hydrogen peroxide, formalin, glutaraldehyde, and/or peracetic acid.

14. A sterilization indicator, comprising:
a first compartment containing a genetically engineered biological indicator, the first compartment being adapted to permit the biological indicator to be brought into contact with a sterilization medium during sterilization; and
a second compartment containing at least one enzyme substrate, the second compartment being adapted to maintain the enzyme substrate separate from the biological indicator during sterilization, and the second compartment being adapted to permit the enzyme substrate to contact the biological indicator after the biological indicator has been exposed to the sterilization medium;
wherein the genetically engineered biological indicator comprises spores of *Geobacillus stearothermophilus* and/or *Bacillus atrophaeus* and at least one reporter gene selected from lacZ, bgaB, xylE and cat for producing an indicator enzyme, the reporter gene being taken up by the spores of *Geobacillus stearothermophilus* and/or *Bacillus atrophaeus*;
wherein the spores of *Geobacillus stearothermophilus* and/or *Bacillus atrophaeus* in the sterilization indicator are free of any active or activatable repressor gene that would inhibit expression of the reporter gene if present in the test organism or sterilization indicator, and
wherein the indicator enzyme and the enzyme substrate are selected such that enzymatic action of the indicator enzyme upon the enzyme substrate yields a detectable signal.

15. The sterilization indicator of claim 14 wherein the indicator enzyme comprises beta-D-galactosidase, beta-D-glucosidase, alpha-D-glucosidase, alkaline phosphatase, acid phosphatase, butyrate esterase, caprylate esterase lipase, chloroamphenicol acetytransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof.

* * * * *